US011882886B2

(12) United States Patent
Murrietta et al.

(10) Patent No.: US 11,882,886 B2
(45) Date of Patent: Jan. 30, 2024

(54) ATHLETIC SOCK (71) Applicant: NIKE, Inc., Beaverton, OR (US)

(72) Inventors: Trina Z. Murrietta, Portland, OR (US); Asli E. Whitham, Hillsboro, OR (US); Ronen Yehuda, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 17/525,640

(22) Filed: Nov. 12, 2021

(65) Prior Publication Data
US 2022/0202105 A1 Jun. 30, 2022

Related U.S. Application Data (60) Provisional application No. 63/164,677, filed on Mar. 23, 2021, provisional application No. 63/157,890, filed on Mar. 8, 2021, provisional application No. 63/132,593, filed on Dec. 31, 2020.

(51) Int. Cl.
| | |
|---|---|
| A41B 11/02 | (2006.01) |
| A41B 11/00 | (2006.01) |
| D04B 1/26 | (2006.01) |
| D03D 1/00 | (2006.01) |
| A61F 2/78 | (2006.01) |
| D04B 1/18 | (2006.01) |
| D04B 1/10 | (2006.01) |

(52) U.S. Cl.
CPC ............ *A41B 11/02* (2013.01); *A41B 11/003* (2013.01); *A61F 2/7812* (2013.01); *D03D 1/0043* (2021.05); *D04B 1/102* (2013.01); *D04B 1/18* (2013.01); *D04B 1/265* (2013.01); *A61F 2002/7837* (2013.01); *D10B 2401/041* (2013.01); *D10B 2509/00* (2013.01)

(58) Field of Classification Search
CPC ......... A41B 11/02; A41B 11/04; A41B 11/12; A41B 11/121; A41B 11/123; A41B 11/003; D04B 1/26
USPC ...................................................... 2/240, 241
See application file for complete search history.

(56) References Cited

U.S. PATENT DOCUMENTS

| | | |
|---|---|---|
| 1,806,492 A | 5/1931 | Nestler |
| 2,050,535 A | 8/1936 | Martel |
| 2,102,368 A | 12/1937 | Martel |

(Continued)

FOREIGN PATENT DOCUMENTS

| | | |
|---|---|---|
| DE | 20219015 U1 | 4/2003 |
| EP | 2815728 B1 | 1/2016 |

(Continued)

OTHER PUBLICATIONS

International Search Report and Written Opinion for PCT application No. PCT/US2021/059928, dated Feb. 25, 2022, 19 pages.

(Continued)

*Primary Examiner* — Jocelyn Bravo
(74) *Attorney, Agent, or Firm* — SHOOK, HARDY & BACON L.L.P.

(57) ABSTRACT

Aspects herein are directed to a knit sock having a leg portion and an integrally knit ankle welt extending around a circumference of the leg portion and positioned at a lower end of the leg portion. The knit sock further includes an integrally knit tab located at a back aspect of the ankle welt.

17 Claims, 9 Drawing Sheets (56) References Cited

U.S. PATENT DOCUMENTS

| | | | |
|---|---|---|---|
| 2,279,919 A | 4/1942 | Harry | |
| 2,926,512 A | 3/1960 | Robertson | |
| 3,130,566 A * | 4/1964 | Chesebro | A41B 11/00 |
| | | | 66/171 |
| 3,601,818 A | 8/1971 | Chesebro et al. | |
| 3,793,851 A | 2/1974 | Thorneburg | |
| 3,975,929 A | 8/1976 | Fregeolle | |
| 3,991,424 A | 11/1976 | Prahl | |
| 4,034,580 A * | 7/1977 | Holder | D04B 1/106 |
| | | | 66/172 E |
| 4,034,581 A | 7/1977 | Swafford | |
| 4,038,699 A | 8/1977 | Burn | |
| 4,149,274 A | 4/1979 | Garrou et al. | |
| 4,237,707 A | 12/1980 | Coble et al. | |
| 4,282,727 A | 8/1981 | Dunlap et al. | |
| 4,282,728 A | 8/1981 | Tapp et al. | |
| 4,326,393 A | 4/1982 | Dunlap | |
| 4,341,096 A | 7/1982 | Safrit et al. | |
| 4,494,388 A | 1/1985 | Lau et al. | |
| 4,514,863 A | 5/1985 | Tuyet-van | |
| 4,520,635 A | 6/1985 | Shields et al. | |
| 4,522,044 A | 6/1985 | Lineberry et al. | |
| 4,702,091 A * | 10/1987 | Good | D04B 15/06 |
| | | | 66/194 |
| 4,732,015 A * | 3/1988 | Abrams | D04B 15/61 |
| | | | 66/185 |
| 5,307,522 A * | 5/1994 | Throneburg | D04B 1/26 |
| | | | 2/241 |
| 5,335,517 A | 8/1994 | Throneburg et al. | |
| 5,412,957 A | 5/1995 | Bradberry et al. | |
| 5,428,975 A * | 7/1995 | Lee, III | D04B 1/106 |
| | | | 66/172 R |
| 5,603,232 A * | 2/1997 | Throneburg | D04B 1/02 |
| | | | 66/178 R |
| 5,708,985 A * | 1/1998 | Ogden | D04B 1/04 |
| | | | 66/178 R |
| 5,809,575 A | 9/1998 | Chen | |
| 5,931,872 A | 8/1999 | Lohmann | |
| 6,079,235 A | 6/2000 | Schmidt | |
| 6,149,690 A | 11/2000 | Belzidsky | |
| 6,324,874 B2 | 12/2001 | Fujimoto | |
| 6,708,342 B2 | 3/2004 | Boersema | |
| 6,871,516 B2 | 3/2005 | Peeler et al. | |
| D503,802 S | 4/2005 | Bjarnason | |
| 6,964,688 B1 | 11/2005 | Kania | |
| 7,076,973 B1 | 7/2006 | Chesebro et al. | |
| 7,169,189 B2 | 1/2007 | Bjarnason et al. | |
| D590,590 S | 4/2009 | Bonzagni et al. | |
| 7,677,061 B2 * | 3/2010 | Mori | D04B 1/26 |
| | | | 66/185 |
| 7,699,195 B2 | 4/2010 | Scott | |
| 7,748,240 B1 | 7/2010 | Cherneski | |
| D634,925 S | 3/2011 | Gesser et al. | |
| D643,207 S | 8/2011 | Hollingsworth et al. | |
| 8,051,498 B2 | 11/2011 | Ganzoni et al. | |
| 8,220,077 B1 | 7/2012 | Ott et al. | |
| 8,544,300 B2 | 10/2013 | Kaneda et al. | |
| D740,014 S | 10/2015 | Amis | |
| D747,601 S | 1/2016 | Middleton | |
| 9,301,552 B2 | 4/2016 | Dickson | |
| 9,358,172 B2 | 6/2016 | Collins et al. | |
| D762,057 S | 7/2016 | Hakeem | |
| D773,798 S | 12/2016 | Amis | |
| D776,913 S | 1/2017 | Hakeem | |
| 9,603,748 B2 | 3/2017 | Valois et al. | |
| 10,011,926 B2 | 7/2018 | Gaither | |
| 10,271,968 B2 | 4/2019 | Bache et al. | |
| 10,376,391 B2 | 8/2019 | Halldorsson et al. | |
| 10,501,874 B2 | 12/2019 | Kostian | |
| D895,264 S | 9/2020 | Manning et al. | |
| 11,401,636 B2 * | 8/2022 | Amis | A41B 11/004 |
| 2005/0149202 A1 | 7/2005 | Schaffer et al. | |
| 2007/0162153 A1 | 7/2007 | Barnes et al. | |
| 2008/0034478 A1 | 2/2008 | Patterson | |
| 2008/0041113 A1 * | 2/2008 | Mori | D04B 1/26 |
| | | | 66/171 |
| 2009/0031582 A1 | 2/2009 | Lu | |
| 2009/0076625 A1 | 3/2009 | Groves et al. | |
| 2009/0132056 A1 | 5/2009 | Kania | |
| 2009/0158504 A1 | 6/2009 | Sparrow et al. | |
| 2011/0191942 A1 | 8/2011 | Villalobos | |
| 2011/0277218 A1 * | 11/2011 | Padilla | D04B 1/02 |
| | | | 2/239 |
| 2012/0167276 A1 | 7/2012 | Brosie et al. | |
| 2012/0324961 A1 | 12/2012 | Clemendot | |
| 2014/0304895 A1 | 10/2014 | Stuart | |
| 2014/0311187 A1 | 10/2014 | Amarasiriwardena et al. | |
| 2015/0033447 A1 | 2/2015 | Riaz | |
| 2015/0264995 A1 | 9/2015 | Hilderbrand, IV | |
| 2016/0120233 A1 | 5/2016 | Van Tiel et al. | |
| 2016/0278442 A1 | 9/2016 | Moran | |
| 2016/0340813 A1 * | 11/2016 | Amis | A41B 11/003 |
| 2017/0000216 A1 | 1/2017 | Dua et al. | |
| 2017/0035120 A1 | 2/2017 | Ramsey et al. | |
| 2017/0216058 A1 | 8/2017 | Dias et al. | |
| 2017/0273363 A1 | 9/2017 | Patchin et al. | |
| 2017/0295851 A1 | 10/2017 | Thibodeau | |
| 2017/0311650 A1 | 11/2017 | Hupperets et al. | |
| 2019/0029331 A1 * | 1/2019 | Field | A41B 11/003 |
| 2019/0037967 A1 | 2/2019 | Mcfarland et al. | |
| 2019/0104780 A1 | 4/2019 | Pinto Rodrigues | |
| 2020/0080242 A1 | 3/2020 | Dardinski et al. | |
| 2020/0100920 A1 | 4/2020 | Finke | |
| 2020/0179140 A1 | 6/2020 | Valois et al. | |
| 2020/0205484 A1 * | 7/2020 | Yehuda | A41B 11/002 |
| 2020/0221791 A1 | 7/2020 | Gazit et al. | |
| 2020/0297514 A1 | 9/2020 | Prescott et al. | |
| 2020/0308738 A1 | 10/2020 | Lineberry et al. | |
| 2020/0347530 A1 | 11/2020 | Tannebaum | |
| 2021/0068471 A1 * | 3/2021 | Giorgi | A41B 11/00 |
| 2021/0071329 A1 * | 3/2021 | Cummings | D04B 21/16 |

FOREIGN PATENT DOCUMENTS

| | | |
|---|---|---|
| EP | 3330419 A1 | 6/2018 |
| FR | 2879405 B1 | 4/2007 |
| GB | 2271923 A | 5/1994 |
| JP | 2007-239129 A | 9/2007 |
| JP | 2009-97122 A | 5/2009 |
| WO | 2004/052132 A1 | 6/2004 |
| WO | 2007/031790 A2 | 3/2007 |
| WO | 2012/006654 A1 | 1/2012 |
| WO | 2012/160834 A1 | 11/2012 |
| WO | 2018/226194 A1 | 12/2018 |
| WO | 2019/028347 A1 | 2/2019 |

OTHER PUBLICATIONS

International Search Report and Written Opinion received for PCT Patent Application No. PCT/US2021/059920, dated Feb. 22, 2022, 16 pages.

Invitation to Pay Additional Fees received for PCT Patent Application No. PCT/US2021/059939, mailed on Mar. 14, 2022, 15 pages.

International Search Report and Written Opinion received for PCT Patent Application No. PCT/US2021/059939, dated May 6, 2022, 21 pages.

Non-Final Office Action received for U.S. Appl. No. 17/525,623, dated Oct. 6, 2022, 9 pages.

A/K Brim Sheath, Knit-Rite, knitrite.com, Available online at: <http://www.knitrite.com/prosthetics/sheaths/brimsheath.html>, Nov. 2, 2012, 2 pages.

Above-Knee Amputee Prosthetic Brim Sheath by GlideWear. Protects Skin from Irritation, Rubbing, Pain, GlideWear, amazon.com, ASIN: B01A5U0G2Q, Nov. 25, 2020, 4 pages.

Ez Sox Toddler Boys Socks Non Skid Anti Slip Grip Seamless Toe Pull Up Loops, Ez Sox, Amazon, ASIN: B01HPAA3G8, Available online at: <https://www.amazon.com/Ez-Sox-Toddler-Boys-Seamless/dp/B01HPAA3G8>, Accessed on Apr. 11, 2019, pp. 1-9.

(56) References Cited

OTHER PUBLICATIONS

Five Things to Know About Nike's New NBA Socks, Nike News, nike.com, Available on Internet at: <https://news.nike.com/news/nba-socks>, Sep. 15, 2017, 11 pages.

Guardian Liner, ALPS&trade, Available online at: <https://easyliner.jp/wp-content/uploads/2018/09/Guardian-Liner_EN.pdf>, Nov. 25, 2020, 2 pages.

Home: TRUSOX®-Performance Enhancing Socks, Trusox, trusox.com, Available on Internet at: <https://web.archive.org/web/20130814050226/http://www.trusox.com>, Aug. 14, 2013, 2 pages.

Liner—Cushion Smart Seal—Above Knee, ALPS™, amputeedepot.com, Available online at: <https://amputeedepot.com/products/alps-smart-seal-cushion-liner-above-knee>, Nov. 25, 2020, 5 pages.

Ronnox Women's Cushioned Anti-Skid Non-Slip Silicone-Gripper Socks, For Yoga Pilates & Barre (Fits Women's Shoe Size 8-14), Amazon, amazon.com, ASIN: B071W2JXXR, Available on Internet at :<htlps://www.amazon.com/dp/B071W2JX XR>, Oct. 26, 2017, 5 pages.

Socks With Loops, Active Hands, Available online at: <https://www.activehands.com/product/socks-with-loops/>, Accessed on Apr. 11, 2019, pp. 1-4.

Stella McCartney: Black Loop Sock Sneakers, SSense, 191471F127002, Available online at: <ssense.com>, Accessed on Apr. 11, 2019, pp. 1-6.

ToeSox—Low Rise Grip Socks, T8 Fitness, Available online at: <https://www.t8fitness.com/products/toesox-low-rise-grip-socks>, Accessed on Apr. 11, 2019, pp. 1-2.

VALOR Amputee Sock—Below Knee Mid-Volume Swiftwick, atlantacycling.com, Available online at: <https://www.atlantacycling.com/product/swiftwick-valor-amputee-sock-below-knee-mid-volume-302001-1.htm>, Nov. 25, 2020, 3 pages.

Final Office Action received for U.S. Appl. No. 17/525,623, dated Apr. 27, 2023, 9 pages.

Notice of Allowance Received for U.S Appl. No. 17/525,623, dated Aug. 9, 2023, 5 pages.

International Preliminary Report on Patentability received for PCT Patent Application No. PCT/US2021/059920, dated Feb. 7, 2023, 9 pages.

International Preliminary Report on Patentability received for PCT Patent Application No. PCT/US2021/059928 dated Jul. 13, 2023, 12 pages.

International Preliminary Report on Patentability received for PCT Patent Application No. PCT/US2021/059939 dated Jul. 13, 2023, 13 pages.

* cited by examiner

ATHLETIC SOCK

CROSS-REFERENCE TO RELATED APPLICATIONS

This application, titled, "Athletic Sock," claims the benefit of priority of U.S. App. No. 63/157,890, filed Mar. 8, 2021, and titled "Athletic Sock," U.S. App. No. 63/164,677, filed Mar. 23, 2021, and titled, "Knit Article with Variable Features," and U.S. App. No. 63/132,593, filed Dec. 31, 2020, and titled "Sleeve for an Extremity." The entireties of the aforementioned applications are incorporated by reference herein.

TECHNICAL FIELD

Aspects herein relate to an athletic sock.

BACKGROUND

Traditional athletic socks may be used for a variety of athletic activities. However, traditional athletic socks may lack features such as zoned cushioning, zoned grip, zoned breathability and permeability, and fit features that make them suitable for certain activities such as running including trail running/hiking. Running, including trail running/hiking, poses a number of challenges such as uneven terrain that causes the foot to shift, for example, medially and laterally within the shoe as well as forward and backward within the shoe, debris (e.g., gravel) that may enter into the space between the sock and the foot especially with ankle length socks, sweating and increased temperatures caused by exertion, and compact surfaces which may impact the joints and muscles of the wearer's foot.

SUMMARY

The following clauses represent example aspects of concepts contemplated herein. Any one of the following clauses may be combined in a multiple dependent manner to depend from one or more other clauses. Further, any combination of dependent clauses (clauses that explicitly depend from a previous clause) may be combined while staying within the scope of aspects contemplated herein. The following clauses are examples and are not limiting.

Clause 1. A knit sock comprising: a collar having a perimeter edge around an opening for receiving a wearer's foot; a leg portion extending from the collar; a foot portion extending from the leg portion and terminating at a toe end; an integrally knit ankle welt extending around a circumference of the knit sock and positioned at a lower end of the leg portion; and a tab located at a back aspect of the ankle welt, the tab integrally knit with the ankle welt.

Clause 2. The knit sock according to clause 1, wherein an inner-facing surface of the tab is positioned adjacent to an outer-facing surface of the leg portion.

Clause 3. The knit sock according to any of clauses 1 through 2, wherein the ankle welt has an upper edge and a lower edge, the lower edge integrally knit with the leg portion.

Clause 4. The knit sock according to clause 3, wherein the upper edge of the ankle welt is separate from the leg portion.

Clause 5. The knit sock according to any of clauses 3 through 4, wherein the tab includes a tab base, a tab body extending from the tab base, and a top edge spaced apart from the tab base by the tab body, and wherein the tab base is integrally knit with the upper edge of the ankle welt.

Clause 6. The knit sock according to clause 5, wherein the top edge of the tab is unattached from the leg portion.

Clause 7. The knit sock according to any of clauses 1 through 6, further comprising a heel portion positioned between the leg portion and the foot portion, the heel portion having an Achilles section and a plantar section, wherein the Achilles section is formed from a knit structure having an alternating pattern comprising a first number of knit courses knit with terry loops and a second number of knit courses knit without terry loops.

Clause 8. The knit sock according to clause 7, wherein the first number of knit courses and the second number of knit courses extend from a lateral side to a medial side of the Achilles section.

Clause 9. The knit sock according to any of clauses 1 through 8, further comprising: a first plurality of integrally knit grip strips located on a lateral side of the foot portion; and a second plurality of integrally knit grip strips located on a medial side of the foot portion.

Clause 10. The knit sock according to any of clauses 1 through 9, further comprising: a third plurality of integrally knit grip strips located on a dorsal side of the toe end of the knit sock; and a fourth plurality of integrally knit grip strips located on a plantar side of the toe end of the knit sock.

Clause 11. The knit sock according to any of clauses 1 through 10, further comprising a heel portion positioned between the leg portion and the foot portion, the heel portion having an Achilles section and a plantar section, wherein the plantar section includes a fifth plurality of integrally knit grip strips that extend from a lateral side to a medial side of the plantar part.

Clause 12. A knit sock comprising: a tubular knit body forming a leg portion and a foot portion extending from the leg portion and terminating at a toe end; an ankle welt extending around a circumference of the tubular knit body and positioned between the leg portion and the foot portion, the ankle welt integrally knit with the tubular knit body; and a tab located at a back aspect of the ankle welt, an inner-facing surface of the tab positioned adjacent to an outer-facing surface of the leg portion.

Clause 13. The knit sock according to clause 12, wherein the ankle welt has an upper edge and a lower edge, and wherein the tab is integrally knit with the upper edge of the ankle welt.

Clause 14. The knit sock according to clause 13, wherein the lower edge of the ankle welt is integrally knit with the tubular knit body, and wherein the upper edge of the ankle welt is separate from the leg portion.

Clause 15. The knit sock according to any of clauses 12 through 14, wherein the tab includes a tab base, a tab body extending from the tab base, and a top edge spaced apart from the tab base by the tab body, wherein: the tab base is integrally knit with the ankle welt, and each of the tab body and the top edge of the tab are unattached from the leg portion.

Clause 16. The knit sock according to any of clauses 12 through 15, further comprising a heel portion positioned between the leg portion and the foot portion, the heel portion having an Achilles section and a plantar section, wherein the Achilles section is formed from a knit structure having an alternating pattern comprising a first number of knit courses knit with terry loops and a second number of knit courses knit without terry loops.

Clause 17. The knit sock according to any of clauses 12 through 16, further comprising one or more integrally knit grip strips that are knit with a yarn formed of filaments having a diameter from about 25 nanometers to about 350 nanometers.

Clause 18. A method of knitting a sock comprising: during a single knitting event: knitting a collar having a perimeter edge around an opening for receiving a wearer's foot; knitting a leg portion extending from the collar; knitting a foot portion extending from the leg portion and terminating at a toe end; knitting an ankle welt such that the ankle welt extends around a circumference of the sock and is positioned at a lower end of the leg portion; and knitting a tab located at a back aspect of the ankle welt such that an inner-facing surface of the tab is positioned adjacent to an outer-facing surface of the leg portion.

Clause 19. The method of knitting the sock according to clause 18, further comprising knitting one or more grip strips using a yarn formed of filaments having a diameter from about 25 nanometers to about 350 nanometers.

Clause 20. The method of knitting the sock according to any of clauses 18 through 19, further comprising knitting a heel portion positioned between the leg portion and the foot portion, the heel portion knit to have an Achilles section and a plantar section, wherein the Achilles section comprises a knit structure having an alternating pattern comprising a first number of knit courses knit with terry loops and a second number of knit courses knit without terry loops.

BRIEF DESCRIPTION OF THE DRAWINGS

Examples of aspects herein are described in detail below with reference to the attached drawing figures, wherein.

DETAILED DESCRIPTION

The subject matter of the present invention is described with specificity herein to meet statutory requirements. However, the description itself is not intended to limit the scope of this disclosure. Rather, the inventors have contemplated that the claimed or disclosed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

Traditional athletic socks may be used for a variety of athletic activities. However, traditional athletic socks may lack features such as zoned cushioning, zoned grip, zoned breathability and permeability, and fit features that make them suitable for certain activities such as running including trail running or hiking. Running, including trail running or hiking, poses a number of challenges such as uneven terrain that causes the foot to shift, for example, medially and laterally within the shoe as well as forward and backward within the shoe, debris (e.g., gravel) that may enter into the space between the sock and the foot especially with ankle length socks, sweating and increased temperatures caused by exertion, and compact surfaces which may impact the joints and muscles of the wearer's foot.

Aspects herein are directed to a knit sock that includes different knit structures and different yarn types that facilitates its use across a variety of athletic activities including, for example, running. In an example aspect, the knit sock includes a leg portion. The knit sock includes an integrally knit ankle welt that extends around a circumference of the sock at a lower end of the leg portion of the sock. The ankle welt provides 360-degree cushioning at an area corresponding to where a typical shoe collar abuts a wearer's ankle. This may be useful when a wearer is running on uneven terrain causing the foot to shift within the shoe. In an example aspect, a tab is located at a back aspect of the ankle welt, where the tab is integrally knit with the ankle welt. The tab may provide enhanced cushioning along the wearer's Achilles tendon. In addition, the tab may help with donning the sock and may provide an easy way for the wearer to adjust the positioning of the sock if it shifts during wear.

The knit sock may include additional features that provide zonal cushioning and zonal breathability and/or permeability. For example, the heel portion of the sock may include an Achilles section that is adapted to be positioned adjacent to a wearer's Achilles tendon during wear and a plantar section that is adapted to be positioned adjacent to a wearer's heel during wear. One or more of the Achilles section and the plantar section includes a knit structure having an alternating pattern of knit courses knit with terry loops to provide cushioning and knit courses knit without terry loops to enhance breathability and permeability of the knit sock.

The knit sock may also optionally have zoned grip features. For example, integrally knit grip strips knit using a grip yarn may be strategically located to enhance grip where needed. Some example locations include a dorsal side and a plantar side of a toe end of the sock. Engineering the sock to include grip strips in this area may help prevent the toe area of the foot from shifting during wear. This may be especially useful when a wearer is running or hiking down an incline. With traditional socks lacking grip strips in this area, this type of movement may cause the wearer's toes to slide forward and impact the toe end of the shoe, which may cause discomfort and/or bruising of the wearer's toenails. Integrally knit grip strips may also be positioned on the lateral and medial sides of the foot portion of the sock. Positioning grip strips on the medial and lateral sides of the foot portion of the sock may help to minimize the medial to lateral shifting that may occur when a wearer runs/walks on uneven terrain. Grip strips may be absent from the dorsal midfoot and plantar midfoot portions of the sock in example aspects. Not utilizing grip strips on the dorsal midfoot portion of the sock may allow the wearer's skin to shift slightly during wear which helps to reduce tension or shearing forces to this sensitive area. Not utilizing grip strips on the plantar midfoot portion of the sock allows some movement of the sock against the wearer's foot arch, which reduces tension or shearing forces to this sensitive area as well. Integrally knit grip strips may be positioned on the plantar section of the heel portion of the sock to help prevent the heel from shifting especially when running or hiking in hilly terrain.

In example aspects, the knit sock may optionally include a knit structure at the forefoot of the sock where the knit structure is adapted to be positioned adjacent to the ball of a wearer's foot during wear. The knit structure may provide cushioning, grip, as well as breathability and/or permeability features. In example aspects, the knit structure may include a repeating pattern that has a first number of knit courses of a body yarn and a plating yarn knit in a basic knit stitch with terry loops followed by a second number of knit courses where the body yarn is floated for a first number of stitches and knit for a second number of stitches; the second number of knit courses are integrally knit with the first number of knit courses. In further example aspects, a grip yarn may be used in the knit structure including in the terry loops. Floating the body yarn increases resistance to stretch and increases the allover compression at the forefoot of the sock to provide a close fit. Further, floating the body yarn may increase the breathability and permeability of the knit structure in the float areas since there are fewer knit loops in the float areas which reduces the overall yarn density in these areas. The use of terry loops provides cushioning to this high impact area of the wearer's foot. In addition, using grip yarns in this area helps to stabilize the forefoot within the shoe and thus reduces shifting of the foot during movement.

The features described above may be used in various combinations, including using all of the features, to provide a knit sock that has zoned grip, zoned cushioning, zoned breathability/permeability, and/or enhanced fit features making the knit sock suitable for athletic activities.

As used throughout the disclosure, the term "sock" means a knit tubular structure having an open first end and a closed second end. The sock may be worn on a foot of a wearer. The term "inner-facing surface" means the surface of the sock that is configured to face toward a skin surface of a wearer, and the term "outer-facing surface" means the surface of the sock that faces away from the inner-facing surface and toward an external environment. In example aspects, the inner-facing surface may comprise the technical back of the knit tubular structure and the outer-facing surface may comprise the technical front of the knit tubular structure. In example aspects, the knit sock described herein may comprise a crew sock. The term "crew sock" means a sock that includes a leg portion that extends fully or partially over the calf area of a wearer. The sock may be described as having several portions such as a collar, the leg portion, a heel portion, a foot portion, and a toe end. The collar has a perimeter edge that defines an opening for receiving the wearer's foot when the sock is worn. When worn, the collar may be positioned below the wearer's knee in one example. The leg portion extends from the collar and is configured to fully or partially cover the calf/shin area of the wearer.

The foot portion extends from the leg portion and is configured to cover the wearer's foot. The foot portion, in turn, may include a dorsal side that is configured to cover the dorsum of a wearer's foot, a medial side configured to cover the medial side of the wearer's foot, a lateral side configured to cover the lateral side of the wearer's foot, and a plantar side configured to cover the sole of the wearer's foot. In example aspects, the foot portion may be divided into a toe end configured to cover the toes of the wearer's foot, a forefoot portion that is configured to cover, for example, the area just posterior to the wearer's toes such as the ball of the foot, a midfoot portion configured to cover the middle of the wearer's foot including, for example, the arch area of the wearer's foot, and a hindfoot portion that is configured to cover the posterior part of the wearer's foot. The heel portion of the sock may include a plantar section that covers the plantar surface of the wearer's heel and an Achilles section configured to cover a lower part of the wearer's Achilles tendon. The different areas of the sock described above are intended to represent general areas or proximate locations, are used for reference purposes for the following discussion, and may not be limiting.

Relational terms used when describing the sock such as upper, lower, inferior, superior, anterior, posterior, front, back, and the like refer to the sock being worn by a wearer as intended with the wearer in a standing position and facing forward.

The term "knit course" as used herein refers to a predominantly horizontal row of knit loops (in an upright textile as knit) that are produced by adjacent needles during the same knitting cycle. The knit course may comprise one or more stitch types such as a knit stitch, a held stitch, a float stitch, a tuck stitch, a transfer stitch, and the like as these terms are known in the art of knitting. The term "knit stitch" or "basic knit stitch" as used herein refers to the basic stitch type where the yarn is cleared from the needle after pulling a loop of the yarn from the back to the front of the textile through a previous stitch. Thus, the legs of the stitch appear on the technical face of the knit textile and the top and bottom of the stitch appear on the technical back of the textile. A knit stitch or basic knit stitch as used herein may include terry loops. The term "wale" as used herein is a predominantly vertical column of intermeshed or interlooped knit loops, generally produced by the same needle at successive (but not necessarily all) courses or knitting cycles. The terms "horizontal" and "vertical" are relative to an upright textile as knit in which the heads of knit loops face toward the top of the textile and the course knit first is oriented toward the bottom of the textile.

The term "float stitch" as used herein occurs when no new stitch is formed at a needle. Thus, the float yarn may extend across one or more adjacent wales. The term "terry loops" as used herein refers to loops formed from knit yarns that extend away from the technical face and/or the technical back of a knit textile and is to be given the meaning that is commonly used in the art of knitting. In example aspects, the terry loops extend away from the technical back of the knit sock such that they face toward a skin surface of a wearer. The term "plating" as used herein means a knit construction where one or more body yarns and one or more plating yarns are knit in the same knit stitch using, for instance, a body yarn feeder and one or more plating yarn feeders. The term "laid-in yarn" means a yarn that is incorporated into the knit construction during a knitting cycle without the laid-in yarn being knitted into loops.

Unless otherwise indicated, the body yarn used to knit the knit sock may include a yarn that includes natural fibers/filaments, a yarn that includes man-made fibers/filaments, or a yarn that contains both natural fibers/filaments and man-made fiber/filaments. In one example aspect, the body yarn may include wool fiber/filaments twisted with polyester fiber/filaments. The plating yarn, in example aspects, may include an elastic yarn such as, for example, a spandex yarn covered with nylon. Similarly, the laid-in yarn, in example aspects, may include an elastic yarn such as a LYCRA® yarn covered with nylon.

The term "welt" as used herein generally refers to a knit structure that may include ribbing and/or may be double knit that is used to support or provide structure to a particular area of the sock. In typical constructions, the welt is generally positioned at the collar of the sock. In aspects contemplated herein, the sock may include a collar welt in addition to a welt positioned at an ankle area of the sock (known as an "ankle welt") as described further herein.

The term "integrally knit" as used herein may mean a textile having a yarn from one or more knitted courses being interlooped with one or more knitted courses of another area. For instance, the ankle welt may be integrally knit with, for example, the tubular body of the knit sock if a yarn from the ankle welt is interlooped with a yarn from the tubular body. In another example, the tab may be integrally knit with the ankle welt if a yarn from the tab is interlooped with a yarn from the ankle welt.

Continuing, it is contemplated herein that the grip strips may be knit with a yarn type having grip characteristics, which is known herein as a "grip yarn." The term "grip yarns" used when describing yarns that form the grip strips refer to a yarn having a high number of filaments (e.g., 7000 or greater) per single yarn strand such that the denier per filament of the grip yarn is about 0.01 or less. Stated differently, the grip yarn may be formed of filaments having a diameter from about 25 nanometers to about 350 nanometers. In example aspects, the grip yarn may be formed through an "islands-in-the-sea" process. An example filament that may be used in the grip yarn is NANOFRONT® produced by Teijin Limited with headquarters in Tokyo, Japan. The large number of filaments provides a large surface-to-volume ratio for the yarn, which contributes to the gripping function of the yarn. To describe it differently, the large number of filaments within the yarn causes the yarn to have a higher coefficient of friction as compared to, for example, more typical yarns that incorporate a smaller number of filaments within a single yarn strand such as yarns that incorporate from between, for example, 50 filaments to 500 filaments per yarn. The term "elastic yarn" as used herein refers to the yarn's ability to stretch from about 100% to about 200% of its original length and recover to approximately (e.g., within 5% to 10%) its original length after the stretching force is removed.

Unless indicated otherwise, all measurements provided herein are taken when the sock is at standard ambient temperature and pressure (298.15 K and 100 kPa) and the sock is in a resting state (e.g., an unstretched state).

FIGS. 1 through 5 respectively depict a lateral view, a medial view, a front view, a plantar view, and a rear view of an example knit sock 100 in accordance with aspects herein. The sock 100 is depicted as though worn by a wearer standing with the wearer's heel elevated to better illustrate different features of the sock 100. The sock 100 generally comprises a tubular body 101 having an open end and a closed end. With respect to FIG. 1, which depicts the lateral view of the knit sock 100, the knit sock 100 includes a collar 110 having a perimeter edge 111 that defines an opening 112 for receiving a wearer's foot. In some example aspects, the collar 110 may include a welt as shown. A leg portion 114 extends downward from the collar 110. In example aspects, the leg portion 114 may include a plurality of knit courses that extend circumferentially around the leg portion 114.

Figure 1:
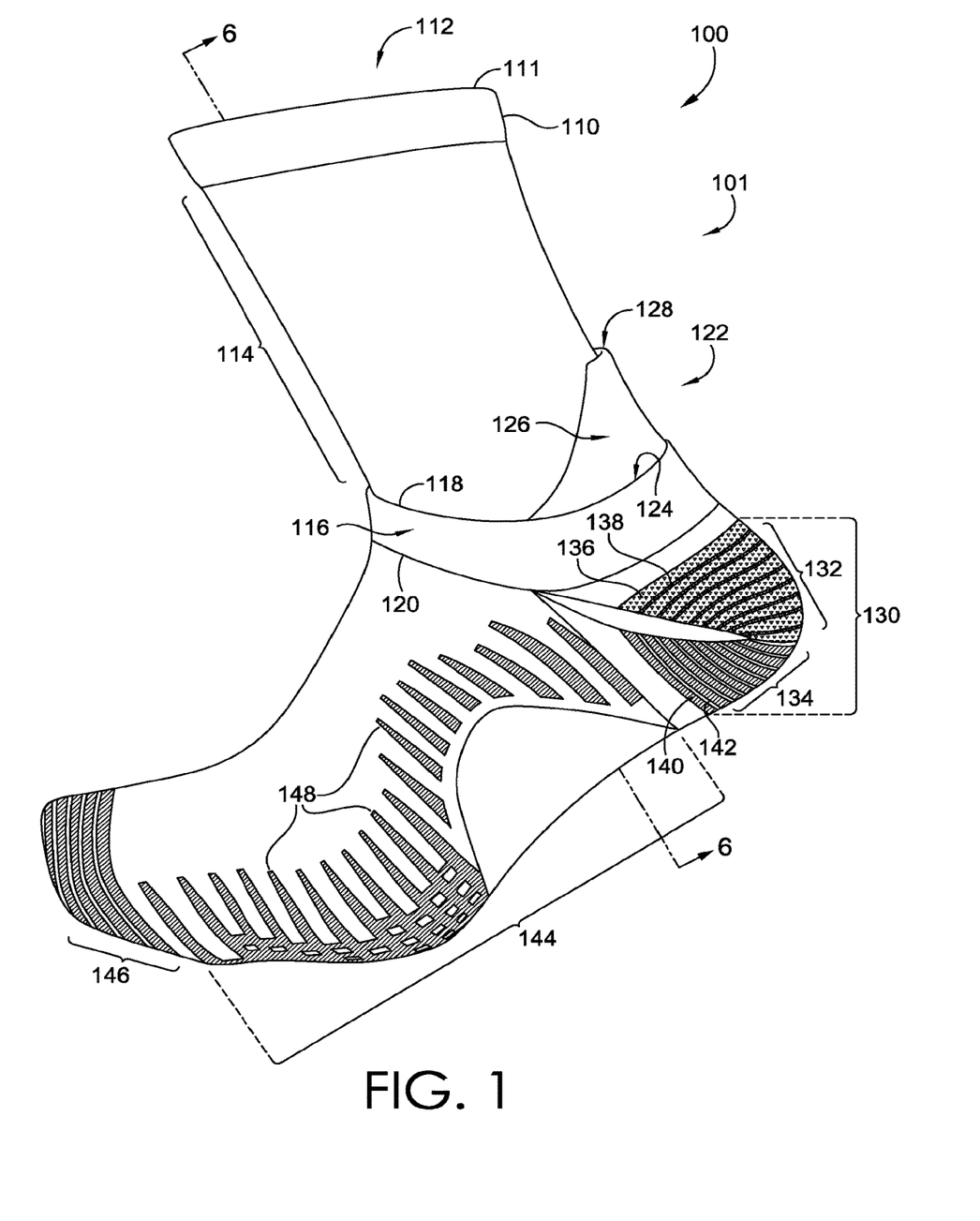
FIG. 1 illustrates a lateral view of an example knit sock in accordance with aspects herein.

The knit sock 100 further includes an ankle welt 116 positioned at a lower end of the leg portion 114 and integrally knit with the leg portion 114. The ankle welt 116 extends around a circumference of the knit sock 100 and includes an upper edge 118 and a lower edge 120. In example aspects, the lower edge 120 is integrally knit with the leg portion 114, and the upper edge 118 is separate from or unattached from the leg portion 114 such that it comprises a free edge. The ankle welt 116 in example aspects may include a ribbed structure and/or may be double knit for extra cushioning, stability, and structure. Positioning the ankle welt 116 such that it extends around an ankle of a wearer when the knit sock 100 is worn and is positioned between a collar of a shoe and the wearer's ankle provides extra cushioning in this area which may be useful when the foot shifts medially and/or laterally during wear as well as forward or backwards.

A tab 122 is positioned at a back aspect of the ankle welt 116 and is integrally knit with the ankle welt 116. In example aspects, the tab 122 may be double knit for extra stability and cushioning. In example aspects, the tab 122 may be knit using a high decitex elastic yarn such as a 156 decitex spandex yarn covered with nylon. In example aspects, the tab 122 may not include a plating yarn or a laid-in yarn. Using a high decitex elastic yarn provides structure to the tab 122 as well as stretch and recovery allowing for easier manipulation of the tab 122 by a wearer.

In an example aspect, the tab 122 includes a tab base 124, a tab body 126 extending from the tab base 124, and a top edge 128 spaced apart from the tab base 124 by the tab body 126 where the top edge 128 is positioned above the tab base 124. In an example aspect, the top edge 128 of the tab 122 may be positioned from about 3 cm to about 5 cm above the tab base 124, from about 3.5 cm to about 4.5 cm above the tab base 124, or about 4 cm above the tab base 124. As used herein, the term "about" means within ±10% of an indicated value. Configuring the tab 122 to have this height ensures that the top edge 128 is positioned so that it extends above the collar of a typical shoe enabling it to be easily grasped by a wearer when adjusting the sock 100. In example aspects, the tab base 124 may be integrally knit with the upper edge 118 of the ankle welt 116. The top edge 128 of the tab 122 may be separate from or unattached from the leg portion 114 of the knit sock 100. As shown the tab 122 tapers as it extends from the tab base 124 to the top edge 128.

Below the ankle welt 116, the knit sock 100 includes a heel portion 130. The heel portion 130 includes an Achilles section 132 and a plantar section 134 where the Achilles section 132 is configured to cover the lower end of a wearer's Achilles tendon and the plantar section 134 is configured to cover the plantar portion of the wearer's heel area. In example aspects, and as described further with respect to FIG. 8, the Achilles section 132 has a knit structure that includes an alternating pattern of a first number of knit courses 136 that are knit with terry loops extending from an inner-facing surface of the knit sock 100 and a second number of knit courses 138 that are knit without terry loops. The first number of knit courses 136 and the second number of knit courses 138 extend from a lateral side to a medial side of the Achilles section 132.

The first number of knit courses 136 may include a greater number of knit courses than the second number of knit courses 138 such that the ratio of the first number of knit courses 136 to the second number of knit courses 138 may be about 2:1. In one example aspect, the first number of knit courses 136 may include from three knit courses to five knit courses or four knit courses, and the second number of knit courses 138 may include from one knit course to three knit courses or two knit courses.

In example aspects, the first number of knit courses 136 may be knit with one type of yarn and the second number of knit courses 138 may be knit with a second type of yarn. For instance, the first number of knit courses 136 may be knit with yarns including natural fibers/filaments such as wool, yarns including synthetic fiber/filaments such as polyester, and/or yarns with a mixture of natural and synthetic fibers/filaments. The second number of knit courses 138 may be knit with an elastic yarn such as a spandex yarn covered with polyester or nylon.

Alternating courses having terry loops with courses not having terry loops provides a desired degree of cushioning while still providing breathability and permeability features. For example, the terry loops provide cushioning, and the areas without terry loops since they have less yarn density, provide breathability and permeability. The ratio of the first number of knit courses 136 to the second number of knit courses 138 may be adjusted as needed to provide more or less cushioning and/or more or less breathability/permeability features. The use of, for instance, wool yarns in the first number of knit courses 136 may contribute to the cushioning features due to the inherent crimp of wool fibers and may also aid in moisture management due to the large moisture regain of wool (e.g., from about 13-18% under standard conditions) which allows the wool yarns to absorb moisture. The use of elastic yarns in the second number of knit courses 138 provides a snug fit around the wearer's Achilles tendon area.

The plantar section 134 of the heel portion 130 may include a similar knit structure comprising an alternating pattern of a first number of knit courses 140 knit with terry loops and a second number of knit courses 142 knit without terry loops as described for the Achilles section 132. As such, the description of the pattern provided with respect to the Achilles section 132 also applies to the plantar section 134. The first number of knit courses 140 and the second number of knit courses 142 extend from a lateral side to a medial side of the plantar section 134. In example aspects, similar to the Achilles section, the second number of knit courses 142 may be knit with an elastic yarn such as a spandex yarn covered with polyester or nylon to provide a snug fit. The first number of knit courses 140 may be knit with a grip yarn as explained further below.

A foot portion 144 extends from the heel portion 130 and the ankle welt 116 to a closed toe end 146 of the knit sock 100. The leg portion 114 in combination with the foot portion 144 forms the tubular body 101 of the knit sock 100. The foot portion 144 includes a plurality of knit courses that extend around the circumference of the knit sock 100. As shown in the lateral view of FIG. 1, the foot portion 144 may include a first plurality of grip strips 148 that are integrally knit with the knit sock 100 using a grip yarn. In example aspects, the first plurality of grip strips 148 are generally positioned on the lateral side of the foot portion 144 of the knit sock 100 such that they do not generally extend on to the dorsal side of the sock or the plantar side of the foot portion 144 of the sock 100. The first plurality of grip strips 148 may include terry loops extending from an inner-facing surface of the knit sock 100. Having the grip yarn form terry loops increases the exposed surface area of the grip yarn to provide a greater level of grip. The first plurality of grip strips 148 may help to stabilize and prevent shifting of the wearer's foot within the shoe especially on uneven terrain.

Figure 3:
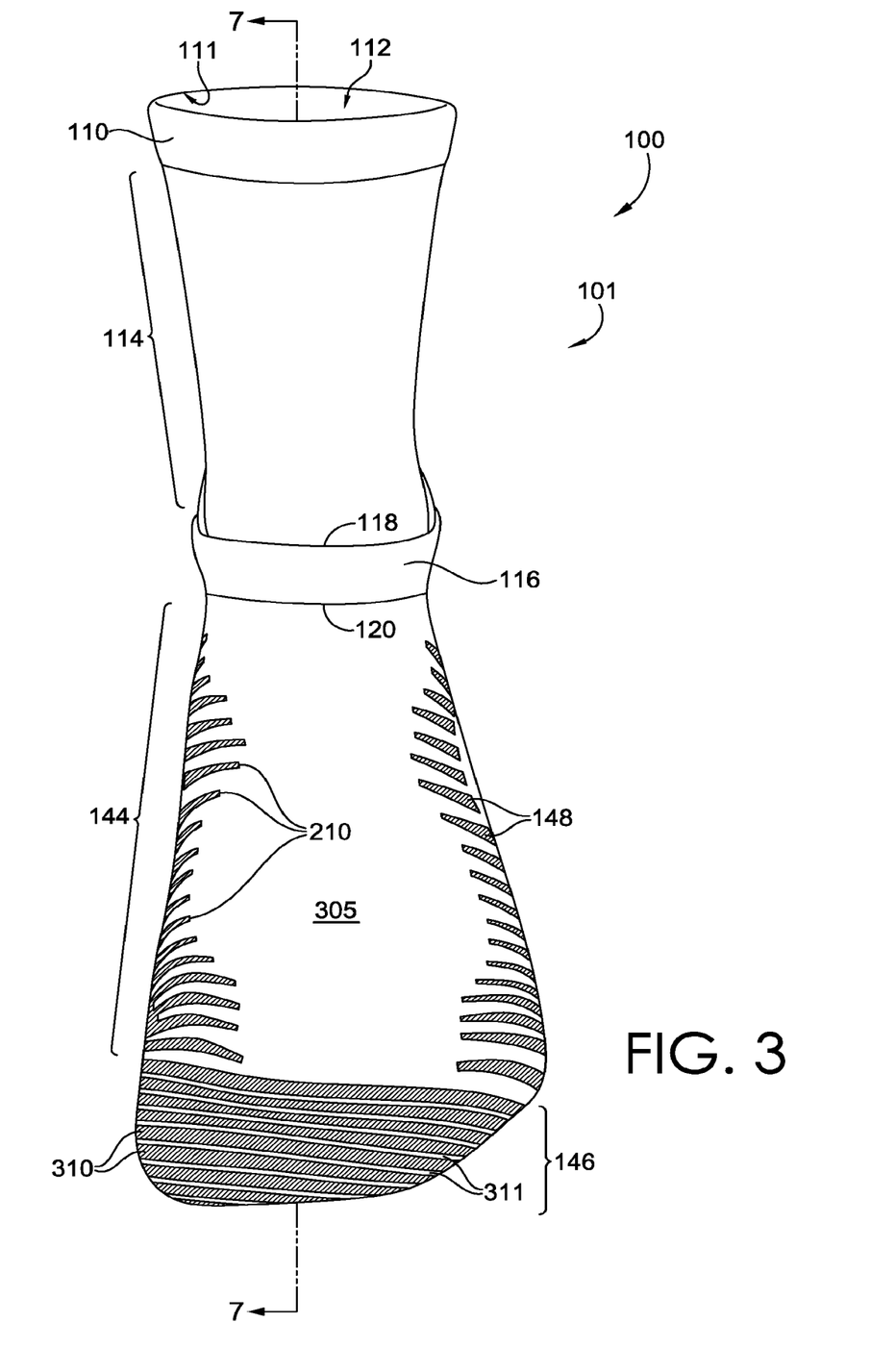
FIG. 3 illustrates a front view of the example knit sock of FIG. 1 in accordance with aspects herein.
Figure 4:
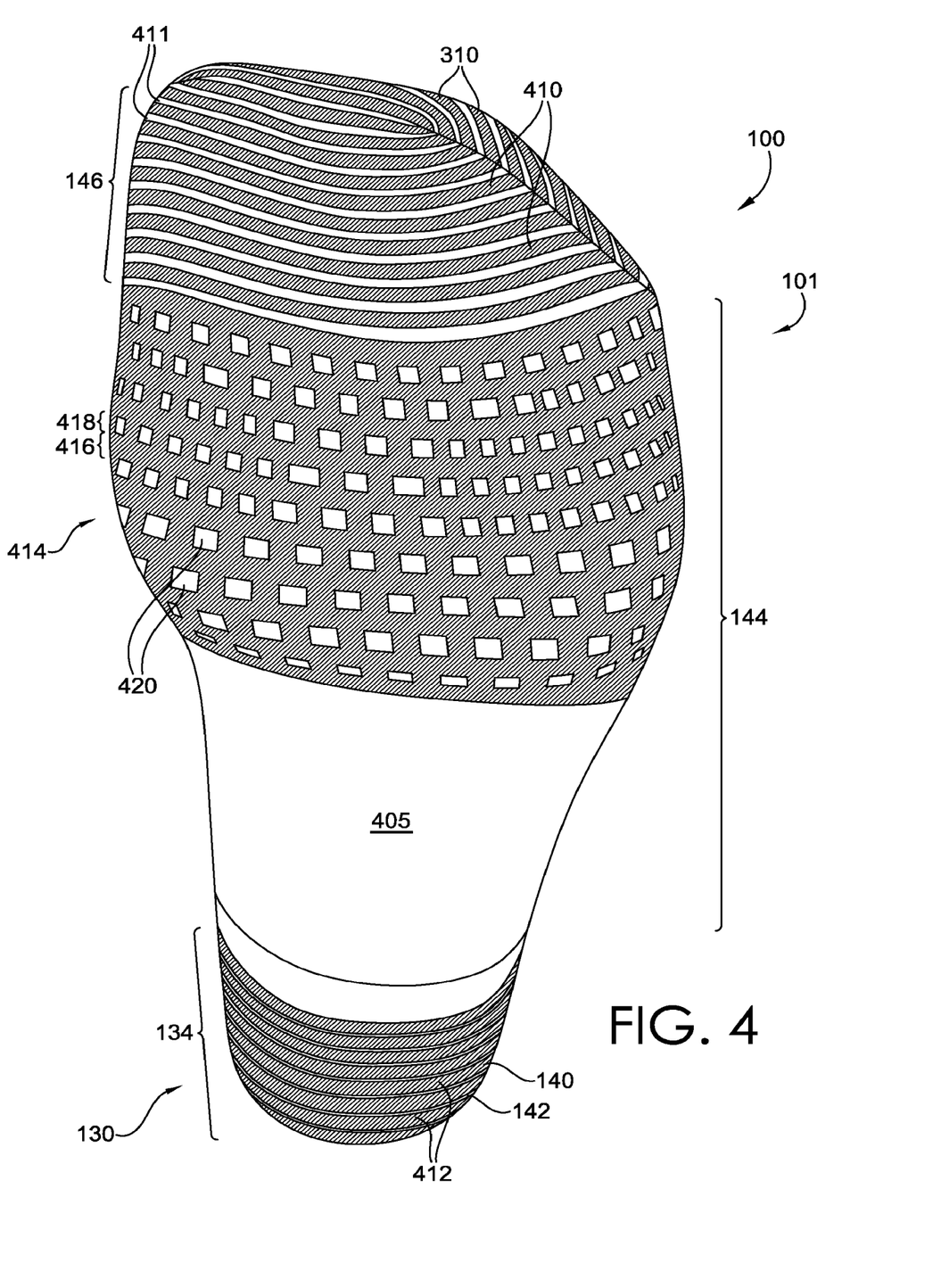
FIG. 4 illustrates a bottom view of the example knit sock of FIG. 1 in accordance with aspects herein.

The toe end 146 of the knit sock 100 may also include grip strips as further described with respect to FIGS. 3 and 4.

Figure 2:
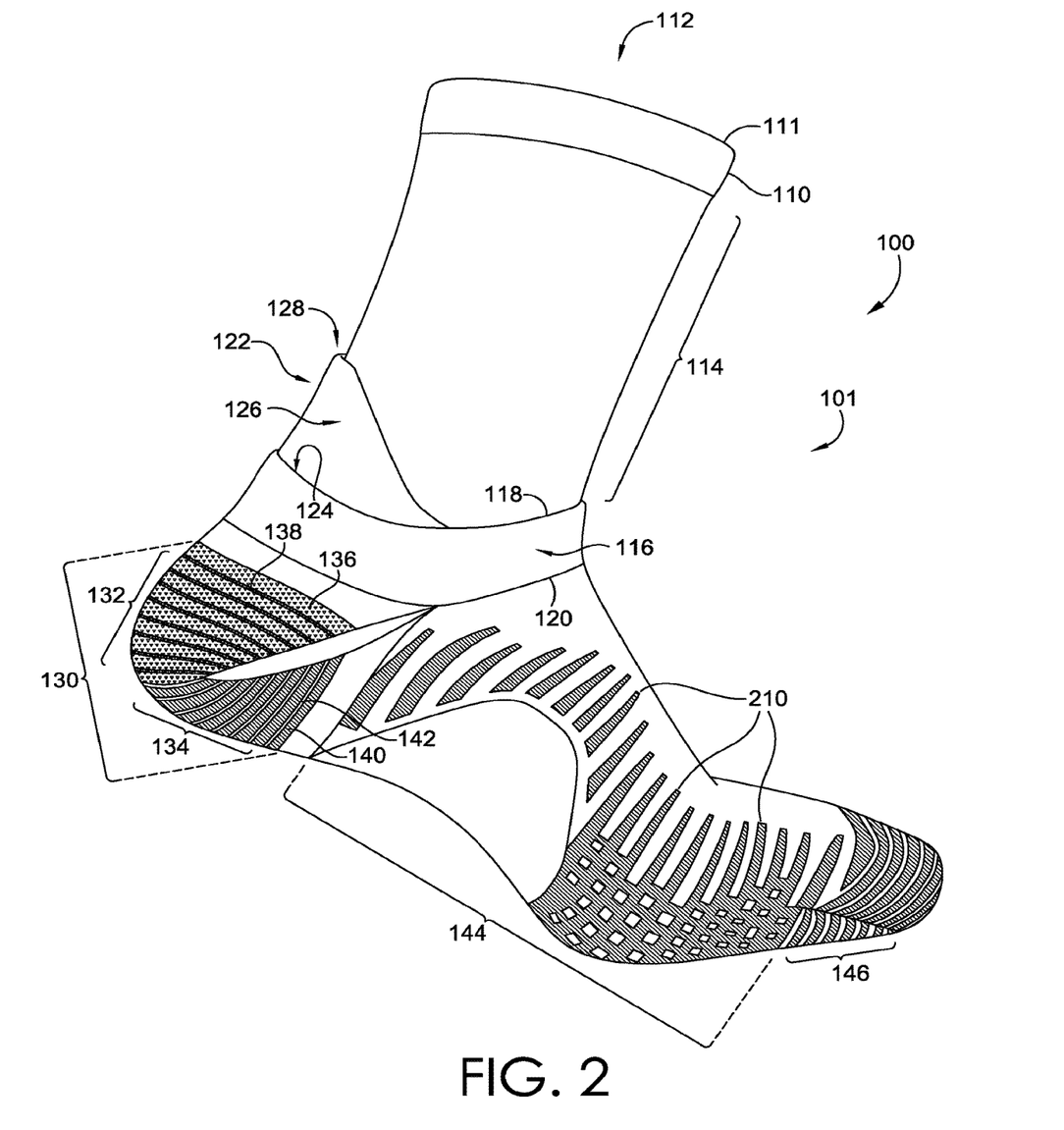
FIG. 2 illustrates a medial view of the example knit sock of FIG. 1 in accordance with aspects herein.

FIG. 2, which depicts a medial view of the knit sock 100 includes many of the same features (indicated with the same reference numerals) as the lateral view as shown in FIG. 1 but from an opposite side of the knit sock 100. As such, the ankle welt 116 is shown extending circumferentially around the knit sock 100, and the tab 122 is shown extending partially around to the medial side of the knit sock 100. Similarly, the first number of knit courses 136 and the second number of knit courses 138 of the Achilles section 132 are shown extending around the medial side of the heel portion 130, and the first number of knit courses 140 and the second number of knit courses 142 of the plantar section 134 are shown extending around the medial side of the heel portion 130.

As shown in the medial view of FIG. 2, the foot portion 144 may include a second plurality of grip strips 210 that are integrally knit with the knit sock 100 using a grip yarn. In example aspects, the second plurality of grip strips 210 are generally positioned on the medial side of the foot portion 144 of the knit sock 100 such that they do not generally extend on to the dorsal side of the sock or the plantar side of the foot portion 144 of the sock 100. The second plurality of grip strips 210 may include terry loops extending from an inner-facing surface of the knit sock 100. Similar to the first plurality of grip strips 148, the second plurality of grip strips 210 may help to stabilize and prevent medial and lateral shifting of the wearer's foot within the shoe especially on uneven terrain. By not having the first plurality of grip strips 148 and the second plurality of grip strips 210 extend on to the dorsal side of the sock 100 and the plantar side of at least the midfoot region of the sock 100, sensitive, thinner skin in this area may move more freely with respect to the inner-facing surface of the knit sock 100 which may lessen shearing or tensioning forces in these areas and improve wearer comfort.

FIG. 3, which depicts a front view of the knit sock 100, illustrates many of the same features as shown in FIGS. 1 and 2. As shown in FIG. 3, the first plurality of grip strips 148 and the second plurality of grip strips 210 do not extend on to the dorsal side, indicated by reference numeral 305, of the foot portion 144 of the knit sock 100. Stated differently, the first plurality of grip strips 148 and the second plurality of grip strips 210 are generally absent from the dorsal side 305 of the knit sock 100.

As shown in FIG. 3, the toe end 146 includes a third plurality of grip strips 310 located on the dorsal side 305 of the sock and extending from the medial side to the lateral side of the toe end 146. The third plurality of grip strips 310 are integrally knit with the knit sock 100 using a grip yarn. In example aspects, the third plurality of grip strips 310 include terry loops formed from the grip yarn and extending from an inner-facing surface of the knit sock 100. The third plurality of grip strips 310 may help prevent a wearer's toes from, for example, shifting forward during athletic activities lessening the chances for damage to the wearer's toenails. Adjacent grip strips in the third plurality of grip strips 310 may be separated by knit courses such as those indicated by reference numeral 311 that are knit using a non-grip yarn such as, for example, the body yarn described above.

FIG. 4 depicts a bottom view of the knit sock 100. The toe end 146 includes a fourth plurality of grip strips 410 located on a plantar side 405 of the knit sock 100 and extending from the medial side to the lateral side of the toe end 146. The fourth plurality of grip strips 410 are integrally knit with the knit sock 100 using a grip yarn. In example aspects, the fourth plurality of grip strips 410 include terry loops formed from the grip yarn and extending from the inner-facing surface of the knit sock 100. The fourth plurality of grip strips 410 in combination with the third plurality of grip strips 310 help to reduce shifting of the wearer's toes during wear. Adjacent grip strips in the fourth plurality of grip strips 410 may be separated by knit courses such as those indicated by reference numeral 411 knit using a non-grip yarn such as, for example, the body yarn described above.

FIG. 4 further depicts the plantar section 134 of the heel portion 130. As described in relation to FIG. 1, the plantar section 134 includes a repeating pattern of the first number of knit courses 140 knit with terry loops and the second number of knit courses 142 knit without terry loops. In example aspect, the first number of knit courses 140 are knit with a grip yarn, such that the first number of knit courses 140 form a fifth plurality of grip strips 412. Positioning the fifth plurality of grip strips 412 on the plantar section 134 of the heel portion 130 helps to lock the wearer's heel in place and prevent shifting during, for example, walking or running on uneven terrain.

FIG. 4 additionally depicts a knit structure, referenced generally by the numeral 414, that is located on the plantar side 405 of a forefoot portion of the foot portion 144 directly posterior to the fourth plurality of grip strips 410 at the toe end 146. When the knit sock 100 is worn, the knit structure 414 is positioned adjacent to the ball of the wearer's foot. As will be described further with respect to FIG. 9, the knit structure 414 may include a repeating pattern that has a first number of knit courses 416 of a body yarn and a plating yarn knit in a basic knit stitch with terry loops followed by a second number of knit courses 418 where the body yarn is floated for a first number of stitches and knit for a second number of stitches. The areas of the knit structure 414 that include the floats are indicated by reference numeral 420. Floating the body yarn increases resistance to stretch and increases the allover compression at this portion of the knit sock 100. Use of the terry loops in the knit structure 414 provides cushioning to this high impact area of the wearer's foot. In addition, because the float areas 420 in the second number of knit courses 418 have a lower yarn density than, for example, areas comprising knit stitches without floats, breathability and permeability in the float areas 420 may be enhanced.

Figure 5:
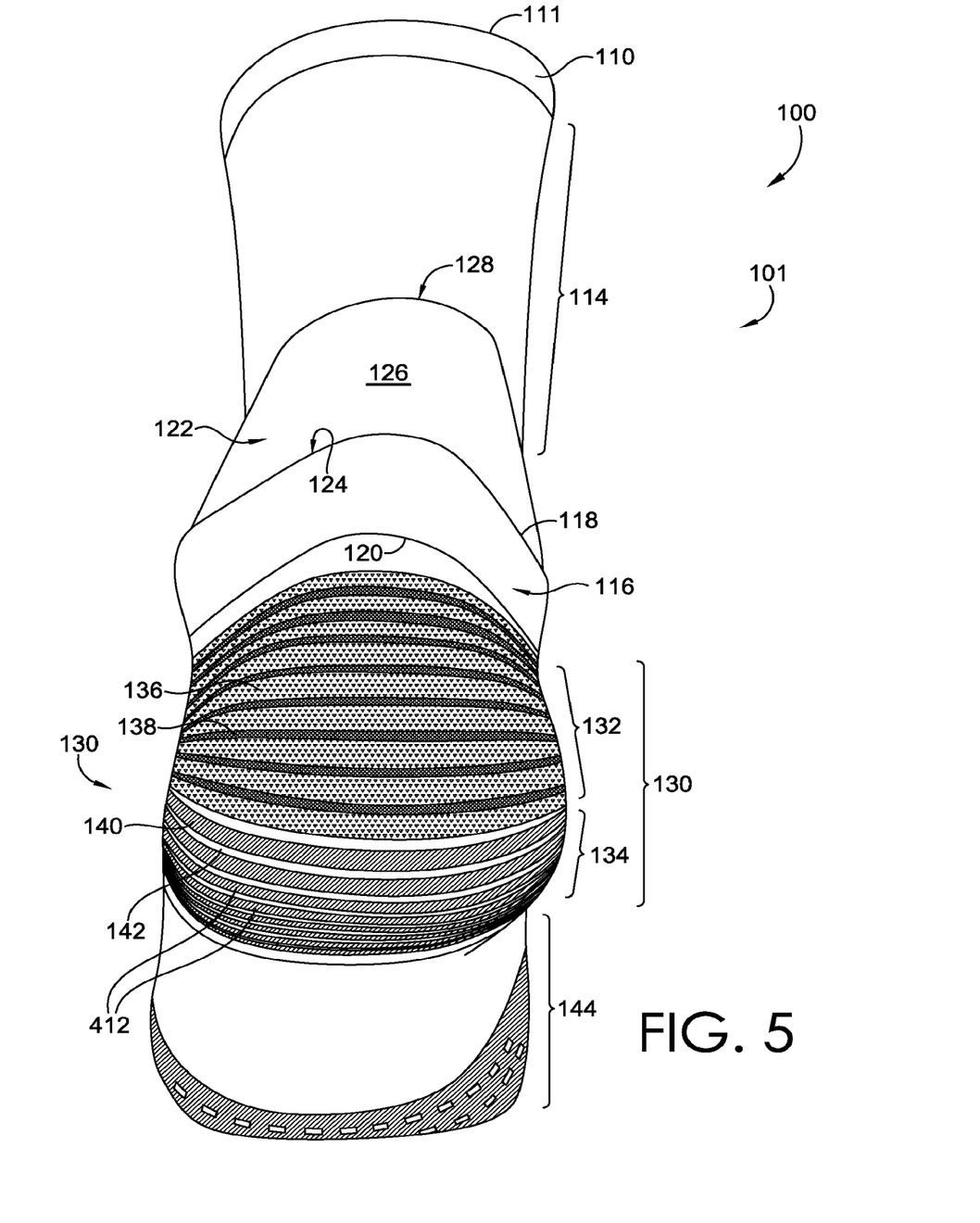
FIG. 5 illustrates a rear view of the example knit sock of FIG. 1 in accordance with aspects herein.

FIG. 5 depicts a rear view of the knit sock 100. As shown, the tab 122 is positioned at the back aspect of the knit sock 100 and extends from a lateral side to a medial side of the knit sock 100. Such positioning allows easy grasping of the tab 122 by a wearer to provide fit adjustment of the knit sock 100 particularly at the ankle area. The Achilles section 132 of the heel portion 130 is depicted with the repeating pattern of the first number of knit courses 136 that include terry loops and the second number of knit courses 138 that do not include terry loops. The plantar section 134 of the heel portion 130 includes the repeating pattern of the first number of knit courses 140 knit with terry loops and the second number of knit courses 142 knit without terry loops where the first number of knit courses 140 are knit with the grip yarn and form the fifth plurality of grip strips 412.

Figure 6:
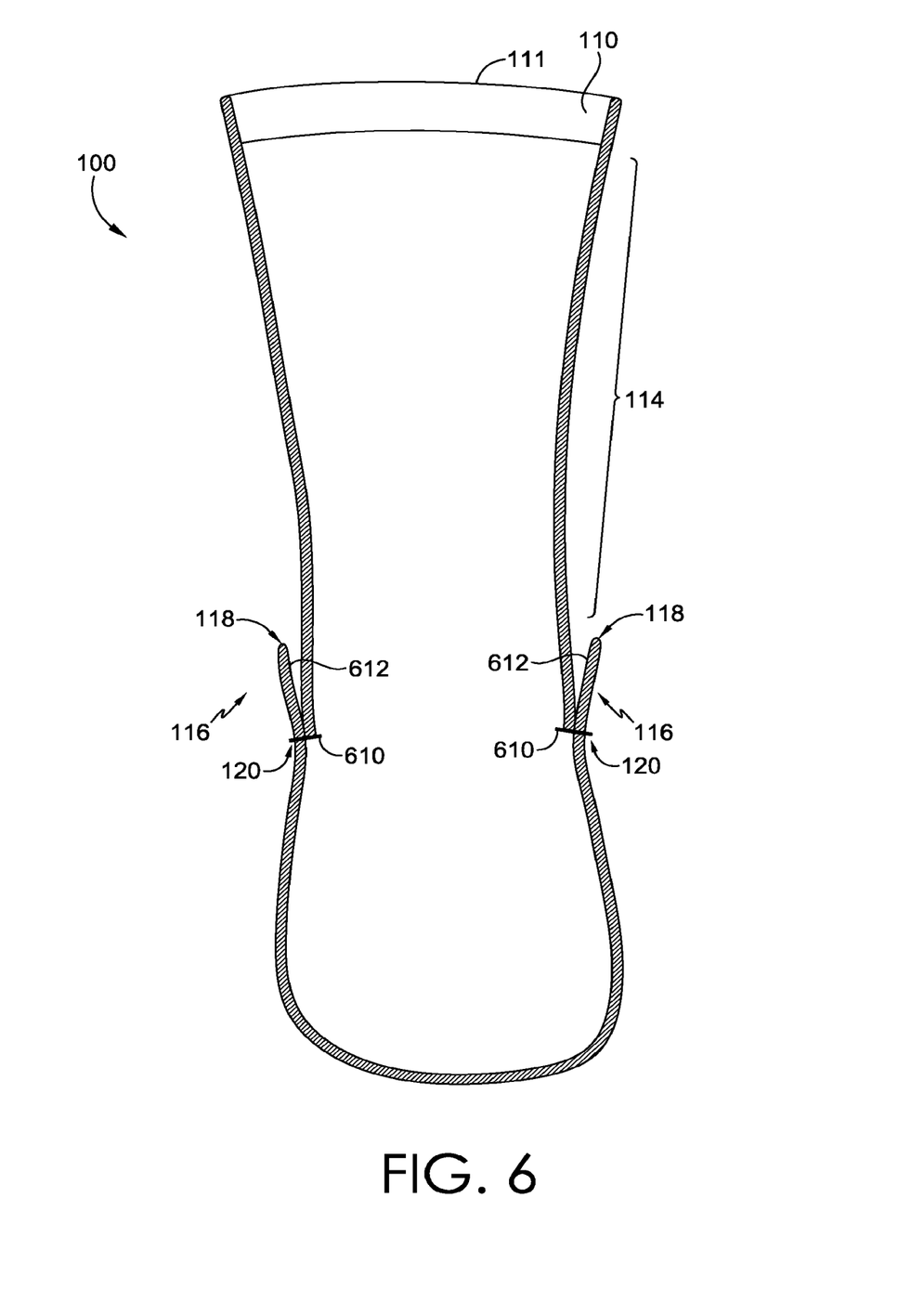
FIG. 6 illustrates a cross-section of the example knit sock taken at cut line 6-6 of FIG. 1 in accordance with aspects herein.

FIG. 6 is a cross-section of the knit sock 100 taken at cut line 6-6 of FIG. 1. FIG. 6 is provided to illustrate how the ankle welt 116 is integrally knit with the knit sock 100 and with the leg portion 114 of the knit sock 100. The lower edge 120 of the ankle welt 116 is integrally knit with the lower end of the leg portion 114 as indicated by the same shading pattern used throughout. Reference numeral 610 schematically depicts a yarn that is interlooped with one or more yarns of the leg portion 114 and one or more yarns of the ankle welt 116. The upper edge 118 of the ankle welt 116 is unattached from or separate from the leg portion 114, and an inner-facing surface 612 of the ankle welt 116 is positioned adjacent and/or faces toward the leg portion 114.

Figure 7:
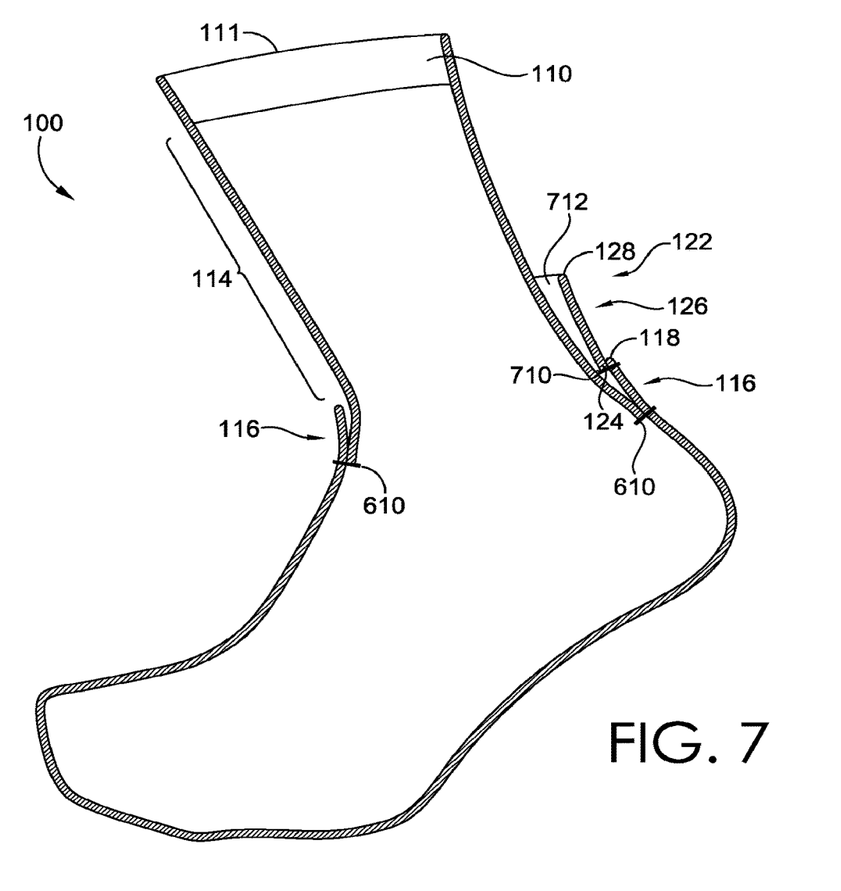
FIG. 7 illustrates a cross-section of the example knit sock taken at cut line 7-7 of FIG. 3 in accordance with aspects herein.

FIG. 7 is a cross-section of the knit sock 100 taken at cut line 7-7 of FIG. 3. FIG. 7 is provided to illustrate how the tab 122 is integrally knit with the ankle welt 116. The tab base 124 is integrally knit with the upper edge 118 of the ankle welt 116. Reference numeral 710 schematically depicts a yarn that is interlooped with one or more yarns of the ankle welt 116 and one or more yarns of the tab 122. The top edge 128 of the tab 122 is unattached from or separate from the leg portion 114, and an inner-facing surface 712 of the tab 122 is positioned adjacent and/or faces toward the leg portion 114.

Figure 8:
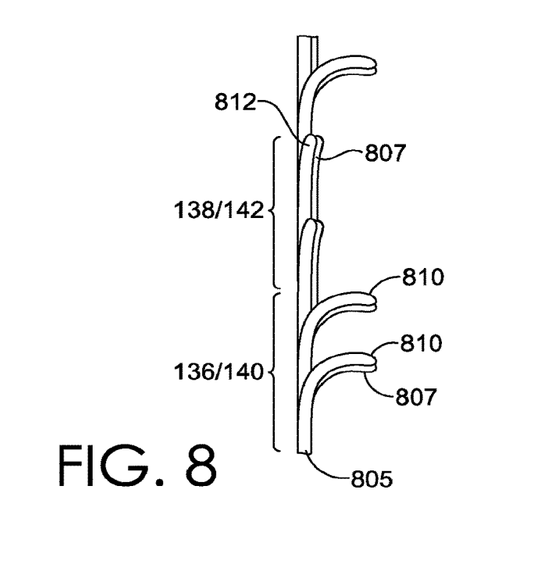
FIG. 8 illustrates a knit schematic of a knit structure located at a heel portion of the example knit sock of FIG. 1 in accordance with aspects herein.

FIG. 8 is an enlarged schematic sectional view illustrating a portion of the knit structure forming, for example, the Achilles section 132 and/or the plantar section 134 of the heel portion 130. The knit structure includes the first number of knit courses 136/140 that are knit with terry loops as indicated by reference numeral 810 and the second number of knit courses 138/142 knit without the terry loops 810. Although not shown, the first number of knit courses 136/140 may include a greater number of knit courses than the second number of knit courses 138/142 such that the ratio of the first number of knit courses 136/140 to the second number of knit courses 138/142 may be about 2:1.

The first number of knit courses 136/140 are knit with a body yarn 805 and a plating yarn 807. With respect to the first number of knit courses 136, the body yarn 805 may include a yarn with natural fibers/filaments such as wool, synthetic fiber/filaments such as polyester, and/or a mixture of natural and synthetic fibers/filaments. With respect to the first number of knit courses 140, the body yarn 805 may include a grip yarn. The plating yarn 807 in the first number of knit courses 136 and the first number of knit courses 140 may include an elastic yarn such as a spandex yarn covered with polyester or nylon.

In some example aspects, the second number of knit courses 138/142 may be knit with a different body yarn 812 than the body yarn 805. For example, with respect to both the second number of knit courses 138 and the second number of knit courses 142, the body yarn 812 may include an elastic yarn such as a spandex yarn covered with polyester or nylon. The same plating yarn 807 may be used for both the second number of knit courses 138 and the second number of knit courses 142.

Figure 9:
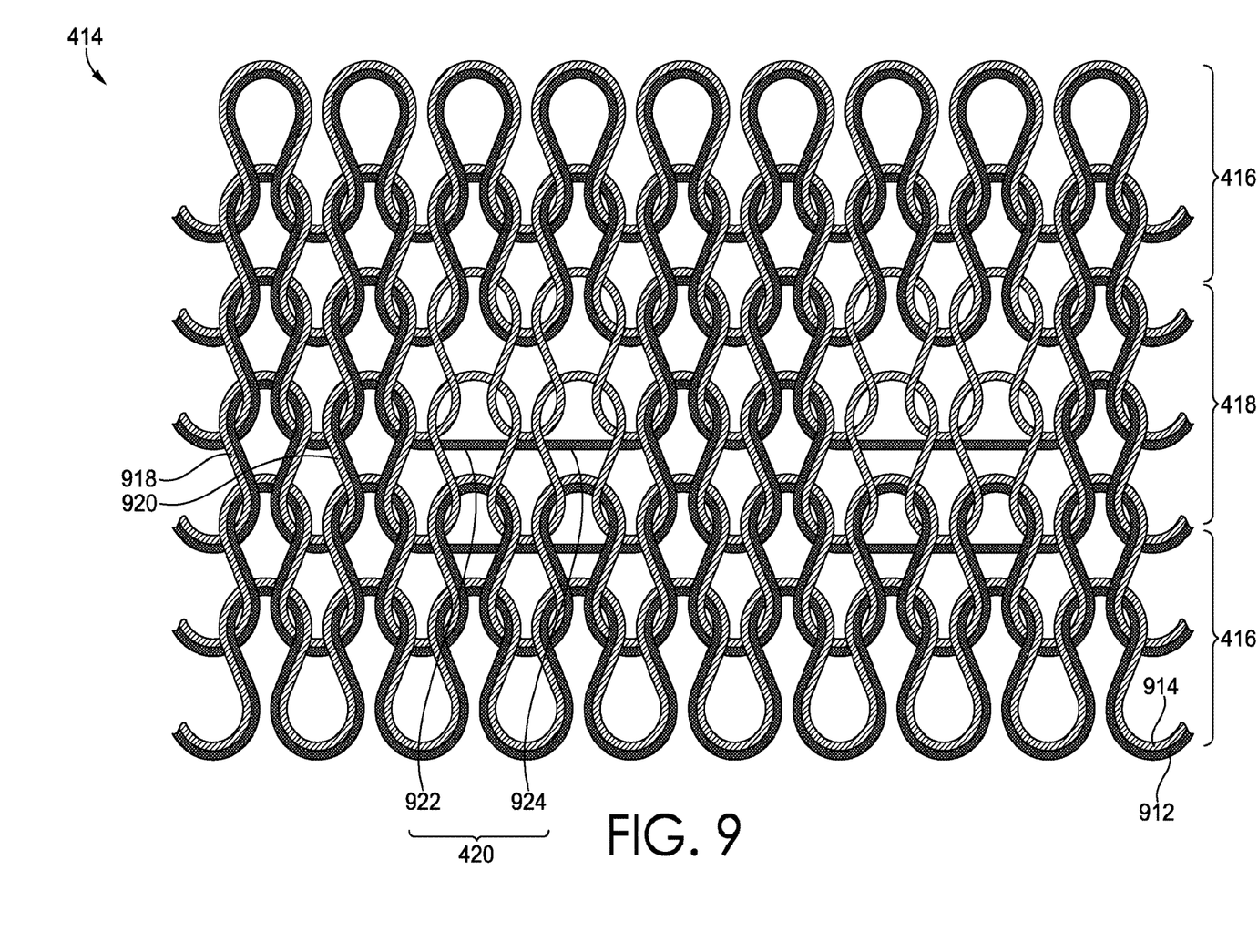
FIG. 9 illustrates a knit schematic of a knit structure located at a forefoot portion of the example knit sock of FIG. 1 in accordance with aspects herein.

FIG. 9 depicts a knit schematic of the knit structure 414 that is located on the plantar side 405 of a forefoot portion of the foot portion 144 directly posterior to the fourth plurality of grip strips 410 at the toe end 146. When the knit sock 100 is worn, the knit structure 414 is positioned adjacent to the ball of the wearer's foot. It is contemplated herein that the knit structure 414 may be used in other locations on the knit sock 100.

The knit structure 414 includes the first number of knit courses 416 knit with a basic knit stitch using at least a body yarn 912 (shown with cross-hatching) and a plating yarn 914 (shown with hatching). In example aspects, the body yarn 912 may include a grip yarn. Although terry loops are not shown, it is contemplated herein that one or more of the body yarn 912 and the plating yarn 914 in the first number of knit courses 416 may be knit to form terry loops on the technical back of the knit structure 414 to provide cushioning as is known in the art of knitting. The first number of knit courses 416 may include two courses as shown. In example aspects, the first number of knit courses 416 may include more than two knit courses such as three knit courses, four knit courses, and the like. Or the first number of knit courses 416 may include a fewer number of knit courses than shown, such as one knit course. The selection of the number of knit courses in the first number of knit courses 416 may be based on desired end properties of the knit structure 414 such as, for example, increased or decreased cushioning.

Next, the knit structure 414 includes the second number of knit courses 418 that have a repeating pattern of two basic knit stitches, such as knit stitches 918 and 920 knit with the body yarn 912 and the plating yarn 914, followed by two float stitches, such as float stitches 922 and 924 to form the float areas 420. In this example aspect, the body yarn 912 is floated across two wales while the plating yarn 914 continues to be knit with a basic knit stitch, followed by two basic knit stitches knit with the body yarn 912 and the plating yarn 914, followed by two float stitches, and so on. Floating at least the body yarn 912 increases the stretch resistance of the knit structure 414 (the knit structure 414 is more resistant to stretch) because there is less yarn available for stretching as compared to a knitted loop. This, in turn, increases the compression of the knit structure 414 which may create a tighter fit at the forefoot portion of the foot portion 144 and prevent shifting or rotating of the knit sock 100. Further, due to decreased yarn density at the float areas 420, breathability and/or permeability in these areas may be increased. Knitting the plating yarn 914 in the float areas 420 increases the structural stability of the knit structure 414.

Although the second number of knit courses 418 is shown comprising two knit courses, it is contemplated herein that the second number of knit courses 418 may include additional knit courses such as three knit courses, four knit courses, and the like. It is further contemplated herein that the second number of knit courses 418 may include the same number of knit courses as the first number of knit courses 416 as shown in FIG. 9. It is also contemplated herein that the second number of knit courses 418 may comprise a fewer number of knit courses than the first number of knit courses 416 or a greater number of knit courses than the first number of knit courses 416. The selection of the number of knit courses in the second number of knit courses 418 may be based on desired end properties of the knit structure 414 such as, for example, increased or decreased resistance to stretch and/or breathability.

It is also contemplated herein that the body yarn 912 may extend over a fewer number of wales or of a greater number of wales than that shown. By extending the body yarn 912 over a fewer number of wales (e.g., one wale), the resistance to stretch and/or breathability may be decreased, and by extending the body yarn over a greater number of wales (e.g., greater than two wales), the resistance to stretch and/or breathability may be increased. It is additionally contemplated that the number of float stitches (two in this example) may differ from the number of basic knit stitches that immediately precede and/or follow the float stitches. Any and all aspects, and any variation thereof are contemplated as being within aspects herein.

The knit structure 414 is a repeating pattern such that the first number of knit courses 416 are repeated as shown in FIG. 9. The repeating pattern thus comprises a first number of knit courses having a basic knit stitch with terry loops, and a second number of knit courses where the body yarn is knit for a first number of stitches and then floated for a second number of stitches.

Figure 10:
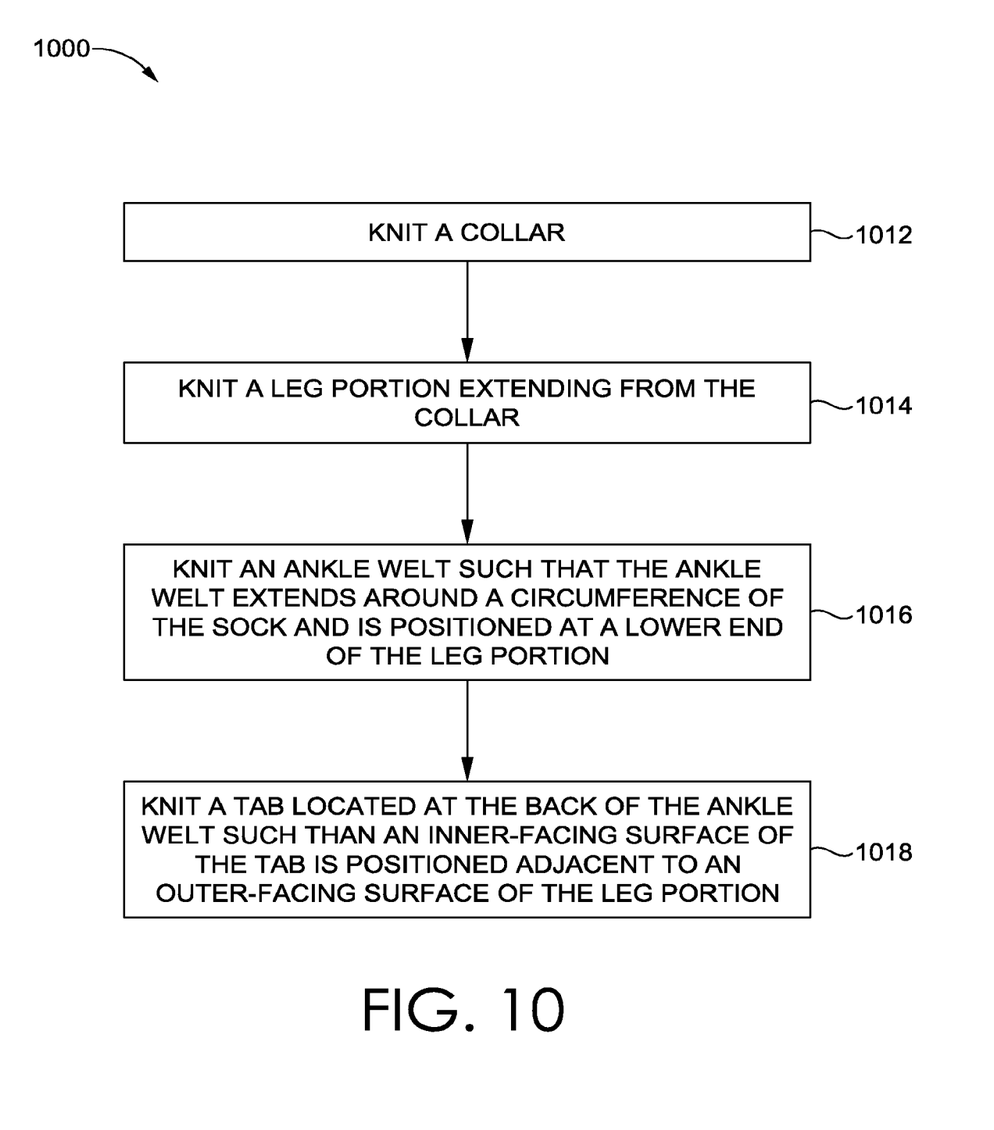
FIG. 10 illustrates a flow diagram of an example method of manufacturing the example knit sock of FIG. 1 in accordance with aspects herein.

FIG. 10 is a flow diagram of an example method 1000 of manufacturing a knit sock such as the knit sock 100. The method 1000 is executed during a single knitting event on a knit machine such as, for example, a circular knit machine configured to knit socks. At a step 1012, a collar, such as the collar 110 is knit where the collar has a perimeter edge around an opening for receiving a wearer's foot. At a step 1014, a leg portion, such as the leg portion 114 is knit where the leg portion extends from the collar. At a step 1018, an ankle welt, such as the ankle welt 116 is knit so that the ankle welt extends around a circumference of the knit sock and is positioned at a lower end of the leg portion. At a step 1020, a tab, such as the tab 122 is knit at a back aspect of the ankle welt. In example aspects, an inner-facing surface of the tab is positioned adjacent to an outer-facing surface of the leg portion.

The method 1000 may include additional steps such as knitting a foot portion (e.g., the foot portion 144) where the foot portion extends from the leg portion. The method 1000 may further include knitting one or more grip strips using a yarn formed of filaments having a diameter from about 25 nanometers to about 350 nanometer. In addition, the method 1000 may include knitting a heel portion, such as the heel portion 130, where the heel portion is located between the leg portion and the foot portion. The heel portion is knit to have an Achilles section, such as the Achilles section 132, and a plantar section, such as the plantar section 134. One or more of the Achilles section and the plantar section may include a knit structure having an alternating pattern comprising a first number of knit courses (e.g., first number of knit courses 136 and 140) knit with terry loops and a second number of knit courses (e.g., second number of knit courses 138 and 142) knit without terry loops.

The knitting steps described above may occur in the order listed but it is contemplated herein that the knitting steps may occur in a different order. For example, a toe end of the knit sock may be knit first.

Aspects of the present disclosure have been described with the intent to be illustrative rather than restrictive. Alternative aspects will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Not all steps listed in the various figures need be carried out in the specific order described.

The invention claimed is:

1. A knit sock comprising:
    a collar having a perimeter edge around an opening for receiving a wearer's foot;
    a leg portion extending from the collar;
    a foot portion extending from the leg portion and terminating at a toe end;
    an integrally knit ankle welt extending around a circumference of the knit sock and positioned at a lower end of the leg portion; and
    a tab located at a back aspect of the ankle welt, the tab integrally knit with the ankle welt; wherein:
        the ankle welt has an upper edge and a lower edge, the lower edge integrally knit with the leg portion; and
        the upper edge of the ankle welt is separate and spaced apart from the leg portion.

2. The knit sock of claim 1, wherein an inner-facing surface of the tab is positioned adjacent to an outer-facing surface of the leg portion.

3. The knit sock of claim 1, wherein the tab includes a tab base, a tab body extending from the tab base, and a top edge spaced apart from the tab base by the tab body, and wherein the tab base is integrally knit with the upper edge of the ankle welt.

4. The knit sock of claim 3, wherein the top edge of the tab is unattached from the leg portion.

5. The knit sock of claim 1, further comprising a heel portion positioned between the leg portion and the foot portion, the heel portion having an Achilles section and a plantar section, wherein at least the Achilles section is formed from a knit structure having an alternating pattern comprising a first number of knit courses knit with terry loops and a second number of knit courses knit without terry loops.

6. The knit sock of claim 5, wherein the first number of knit courses and the second number of knit courses extend from a lateral side to a medial side of the Achilles section.

7. The knit sock of claim 1, further comprising:
a first plurality of integrally knit grip strips located on a lateral side of the foot portion; and
a second plurality of integrally knit grip strips located on a medial side of the foot portion.

8. The knit sock of claim 7, further comprising:
a third plurality of integrally knit grip strips located on a dorsal side of the toe end of the knit sock; and
a fourth plurality of integrally knit grip strips located on a plantar side of the toe end of the knit sock.

9. The knit sock of claim 8, further comprising a heel portion positioned between the leg portion and the foot portion, the heel portion having an Achilles section and a plantar section, wherein the plantar section includes a fifth plurality of integrally knit grip strips that extend from a lateral side to a medial side of the plantar section.

10. A knit sock comprising:
a tubular knit body forming a leg portion and a foot portion extending from the leg portion and terminating at a toe end;
an ankle welt extending around a circumference of the tubular knit body and positioned between the leg portion and the foot portion, the ankle welt integrally knit with the tubular knit body and having an upper edge that is separate and spaced apart from the leg portion; and
a tab located at a back aspect of the ankle welt, an inner-facing surface of the tab positioned adjacent to an outer-facing surface of the leg portion;
wherein the tab is integrally knit with the upper edge of the ankle welt.

11. The knit sock of claim 10, wherein the ankle welt has a lower edge that is integrally knit with the tubular knit body.

12. The knit sock of claim 10, wherein the tab includes a tab base, a tab body extending from the tab base, and a top edge spaced apart from the tab base by the tab body, wherein:
the tab base is integrally knit with the ankle welt, and
each of the tab body and the top edge of the tab are unattached from the leg portion.

13. The knit sock of claim 10, further comprising a heel portion positioned between the leg portion and the foot portion, the heel portion having an Achilles section and a plantar section, wherein at least the Achilles section is formed from a knit structure having an alternating pattern comprising a first number of knit courses knit with terry loops and a second number of knit courses knit without terry loops.

14. The knit sock of claim 10, further comprising one or more integrally knit grip strips that are knit with a yarn formed of filaments having a diameter from about 25 nanometers to about 350 nanometers.

15. A method of knitting a sock comprising:
during a single knitting event:
knitting a collar having a perimeter edge around an opening for receiving a wearer's foot;
knitting a leg portion extending from the collar;
knitting a foot portion extending from the leg portion and terminating at a toe end;
knitting an ankle welt such that the ankle welt extends around a circumference of the sock and is positioned at a lower end of the leg portion; and
knitting a tab located at a back aspect of the ankle welt such that an inner-facing surface of the tab is positioned adjacent to an outer-facing surface of the leg portion;
wherein:
the ankle welt has an upper edge and a lower edge, the lower edge integrally knit with the leg portion; and
the upper edge of the ankle welt is separate and spaced apart from the leg portion.

16. The method of knitting the sock of claim 15, further comprising knitting one or more grip strips using a yarn formed of filaments having a diameter from about 25 nanometers to about 350 nanometers.

17. The method of knitting the sock of claim 15, further comprising knitting a heel portion between the leg portion and the foot portion, the heel portion knit to have an Achilles section and a plantar section, wherein at least the Achilles section comprises a knit structure having an alternating pattern comprising a first number of knit courses knit with terry loops and a second number of knit courses knit without terry loops.

* * * * *